(12) United States Patent
Williams

(10) Patent No.: US 6,448,432 B2
(45) Date of Patent: Sep. 10, 2002

(54) PROCESS FOR THE PRODUCTION OF VINYL ACETATE

(75) Inventor: Bruce Leo Williams, Brough (GB)

(73) Assignee: BP Chemicals Limited, London (GB)

( * ) Notice: Subject to any disclaimer, the term of this patent is extended or adjusted under 35 U.S.C. 154(b) by 0 days.

(21) Appl. No.: 09/877,250

(22) Filed: Jun. 11, 2001

(30) Foreign Application Priority Data

Jun. 14, 2000 (GB) .............................................. 0014583

(51) Int. Cl.$^7$ .............................................. C07C 67/05
(52) U.S. Cl. ...................................................... 560/245
(58) Field of Search ........................................ 560/245

(56) References Cited

U.S. PATENT DOCUMENTS

| | | |
|---|---|---|
| 2,596,748 A | 5/1952 | Watson et al. |
| 2,781,300 A | 2/1957 | Hoge |
| 3,625,998 A | 12/1971 | Fernholz et al. |
| 5,550,281 A | 8/1996 | Cirjak et al. |
| 5,688,993 A | * 11/1997 | Provine et al. |
| 6,103,949 A | * 8/2000 | Demmel |

FOREIGN PATENT DOCUMENTS

| | | |
|---|---|---|
| EP | 0 672 453 A2 | 9/1995 |
| EP | 0 685 449 A1 | 12/1995 |
| EP | 0 685 451 A1 | 12/1995 |
| EP | 0 761 305 A1 | 3/1997 |
| EP | 0 985 655 | 3/2000 |
| EP | 1 006 100 A1 | 6/2000 |
| EP | 1 008 385 A2 | 6/2000 |

* cited by examiner

Primary Examiner—Paul J. Killos
Assistant Examiner—Farhad Forohar
(74) Attorney, Agent, or Firm—Nixon & Vanderhye

(57) ABSTRACT

A process for the fluid bed production of vinyl acetate which comprises reacting ethylene, acetic acid and an oxygen-containing gas in a fluid bed reactor at elevated temperature in the presence of a fluidised bed of catalyst, in which process, catalyst is added to said fluidised bed of catalyst, wherein the overall catalytic activity of the fluidised bed of catalyst is controlled to a pre-determined value by adjusting the activity and/or adjusting the rate of addition of said added catalyst.

18 Claims, 2 Drawing Sheets

PROCESS FOR THE PRODUCTION OF VINYL ACETATE

The present invention relates to a process for the production of vinyl acetate and in particular to a method of controlling the production rate of a fluid bed process for the manufacture of vinyl acetate.

BACKGROUND OF THE INVENTION

It is known that vinyl acetate can be produced in a fluid bed reactor by contacting acetic acid and ethylene with molecular oxygen in the presence of a fluid bed catalyst active for the production of vinyl acetate. Such a process is described for example in EP-A-0672453, EP-A-0685449, EP-A-068545 1, EP-A-0985655 and EP-A-1008385.

It is generally known in such catalytic processes that catalytic activity will decrease with time for various reasons such as metal sintering and as a result, changes in operating conditions are required to maintain the rate of production. Typically, such a decrease in catalytic activity may be partially countered by increasing the temperature of the catalyst bed. However, increasing the temperature of the catalyst bed may result in a decrease in the selectivity of the process. In addition, there is a maximum operating temperature at which the process can be safely carried out. Thus, there is a constraint on the production rate which can be achieved by increasing the temperature of the catalyst bed. Consequently, periodically, it is necessary to shut down the plant and replace the deactivated catalyst with fresh catalyst.

EP-A-0 672 453 describes a process for the fluid bed production of vinyl acetate from ethylene, acetic acid and an oxygen-containing gas in the presence of a palladium promoted catalyst. EP-A-0 672 453 discloses that the continuous addition of make-up catalyst to such a fluid bed vinyl acetate process can maintain peak performance and virtually eliminate catalyst change-outs.

In co-pending application EP 99309222.0 (EP-A-1008385) which relates to a fluid bed process for the manufacture of vinyl acetate it is disclosed that continuous addition of make-up catalyst maintains catalyst performance and eliminates complete change-out and shut-downs.

Thus, there remains a need for an improved fluid bed process for the manufacture of vinyl acetate which avoids or at least mitigates the disadvantages associated with the prior art. It has now been found that the production rate of a fluid bed process for the manufacture of vinyl acetate may be controlled by the addition of fresh catalyst to the fluid bed and/or removal of older catalyst from the fluid bed wherein the activity and/or the rate of addition of any added catalyst is adjusted so as to achieve a desired overall catalyst activity of the fluid bed and hence a desired production rate.

SUMMARY OF THE INVENTION

Thus, according to the present invention there is provided a process for the fluid bed production of vinyl acetate which comprises reacting ethylene, acetic acid and an oxygen-containing gas in a fluid bed reactor at elevated temperature in the presence of a fluidised bed of catalyst, in which process, catalyst is added to said fluidised bed of catalyst, wherein the overall catalytic activity of the fluidised bed of catalyst is controlled to a pre-determined value by adjusting the activity and/or adjusting the rate of addition of said added catalyst.

Generally, if the overall activity of a catalyst bed in a fluid bed process for the manufacture of vinyl acetate is controlled, the production rate of the process may thereby be controlled. The desired production rate in a fluid bed process for the manufacture of vinyl acetate may over time remain constant or may increase or decrease, for example, in response to the market demand for vinyl acetate product.

In accordance with the present invention the overall catalytic activity of a fluidised bed catalyst and hence the production rate of the vinyl acetate process is adjusted to a pre-determined overall level by adjusting the activity and/or adjusting the rate of addition of the added catalyst. Preferably, the overall catalytic activity of a fluidised bed catalyst and hence the production rate of the vinyl acetate process is adjusted to a pre-determined overall level by adjusting the activity and optionally adjusting the rate of addition of the added catalyst.

The added catalyst may have a different activity to that of the initial activity of the catalyst in the fluidised bed. Suitably, the overall catalytic activity of the catalyst bed may be increased by adding catalyst which has a higher activity than that of the initial activity of the catalyst in the fluidised bed. Alternatively, the overall catalytic activity of a fluid bed process for the manufacture of vinyl acetate may be decreased by adding a catalyst which has a lower activity than that of the initial activity of the catalyst in the fluidised bed.

For example, a catalyst having a higher activity than the initial activity of the catalyst in the fluidised bed may be achieved by using a higher active metal loading in the catalyst. Similarly, a vinyl acetate catalyst of lower activity than the catalyst bed may be achieved by using a lower active metal loading. Catalyst having a reduced activity may be added in which the catalyst is diluted with inert support material.

In accordance with the present invention the overall catalytic activity of a fluidised bed of catalyst may be increased, by increasing the rate of addition of any added catalyst to the catalyst bed. Optionally, and in addition to increasing the rate of addition of catalyst to the fluidised bed of catalyst the rate at which deactivated catalyst is removed from the bed may be decreased. Similarly, to decrease the overall catalytic activity of a fluidised bed of catalyst, the rate of addition of any added catalyst to the bed may be decreased. Optionally, and in addition to decreasing the rate of fresh catalyst addition to the catalyst bed the rate at which deactivated catalyst is removed from the catalyst bed may be increased. When the changed rates of addition and optionally removal of the catalyst have achieved the required change in the amount of catalyst in the fluidised bed and hence the required change in overall catalytic activity of the fluidised bed, the rates of addition and removal may be returned to their earlier levels. The amount of catalyst in the reactor should not be reduced below a certain minimum beyond which the reactor will not function. Conversely, the amount of catalyst should not be increased beyond the maximum working level.

The overall catalytic activity of the fluidised bed may also be adjusted by increasing the rate of addition of added catalyst and also increasing the rate of removal of deactivated catalyst thereby reducing the time the catalyst resides in the fluidised bed and hence is subject to deactivation with use. Conversely the rates of addition and removal may be reduced together to adjust the overall catalytic activity.

Rapid changes in the overall activity of the fluidised bed and the overall rate of production may be achieved by changing the reaction conditions such as temperature in addition to adjusting the activity and/or adjusting the rate of addition of the added catalyst. Temperature changes may be achieved more rapidly than catalyst changes and as the catalyst is changed the temperature may be readjusted back to its previous value.

Typically, the catalyst added to the catalyst bed may be fresh catalyst.

Vinyl acetate is generally prepared on a commercial basis by contacting acetic acid and ethylene with a molecular oxygen containing gas in the presence of a catalyst active for the production of vinyl acetate. Hitherto such processes have been operated with a fixed bed of catalyst. Recently, a fluid bed process has been introduced.

In a fluid bed reactor system for the manufacture of vinyl acetate, the particles of the catalyst are maintained in a fluidized state by a suitable gas flow through the system. Excess flow rate may cause channeling of the gas through the reactor which decreases conversion efficiency.

A typical catalyst useful in this invention may have the following particle size distribution:

| | |
|---|---|
| 0 to 20 microns | 0–30 wt % |
| 20 to 44 microns | 0–60 wt % |
| 44 to 88 microns | 10–80 wt % |
| 88 to 106 microns | 0–80 wt % |
| >106 microns | 0–40 wt % |
| >300 microns | 0–5 wt % |

Persons skilled in the art will recognize that support particles sizes of 44, 88, 106 and 300 microns are arbitrary measures in that they are based on standard sieve sizes. Particle sizes and particle size distributions may be measured by an automated laser device such as a Microtrac X100.

In a fluid bed process for the production of vinyl acetate from ethylene, acetic acid and oxygen the ethylene may be used in substantially pure form or admixed with one or more of nitrogen, methane, ethane, carbon dioxide and water in the form of steam or one or more of hydrogen, $C_3/C_4$ alkenes or alkanes.

The oxygen-containing gas may suitably be air or a gas richer or poorer in molecular oxygen than air. Suitably, the gas may be oxygen diluted with a suitable diluent, for example, nitrogen, argon or carbon dioxide. Preferably the gas is oxygen.

The acetic acid may be introduced into the reactor in liquid form or in vapour form.

The process may be carried out in a fluid bed reactor and may suitably be operated at a temperature from 100 to 400° C., preferably 140 to 210° C. and a pressure of $10^5$ to $2\times10^6$ Pa gauge (1 to 20 barg), preferably $6\times10^5$ to $1.5\times10^6$ Pa gauge (6 to 15 barg), especially $7\times10^5$ to $1.2\times10^6$ Pa gauge (7 to 12 barg).

A catalyst suitable for use in the production of vinyl acetate in a fluid bed process may comprise a Group VIII metal, a catalyst promoter and an optional co-promoter.

With regards to the Group VIII metal, the preferred metal is palladium. Suitable sources of palladium include palladium (II) chloride, sodium or potassium tetrachloropalladate, (II), ($Na_2PdCl_4$ or $K_2PdCl_4$), palladium acetate, palladium (II) nitrate or palladium (II) sulphate. The metal may be present in a concentration of greater than 0.2% by weight, preferably greater than 0.5% by weight based upon total weight of catalyst. The metal concentration may be as high as 10% by weight. Generally, the higher the active metal loading in a catalyst suitable for use in vinyl acetate production, the more catalytically active it will be. Thus, for example, a catalyst containing 5 wt % Palladium will be more active than a catalyst which is essentially the same but which has only 0.5 wt % Palladium.

In addition to the Group VIII metal, the catalyst for the production of vinyl acetate comprises a promoter. Suitable promoters include gold, copper, cerium or mixtures thereof A preferred promoter is gold. Suitable sources of gold include gold chloride, tetrachloroauric acid ($HAuCl_4$), $NaAuCl_4$, $KAuCl_4$, dimethyl-gold acetate, barium acetoaurate or gold acetate. The preferred gold compound is $HAuCl_4$. The promoter metal may be present in an amount of from 0.1 to 10% by weight in the finished catalyst.

A catalyst suitable for use in the production of vinyl acetate may comprise a co-promoter material. Suitable co-promoters include Group I, Group II, lanthanide or transition metals, for example cadmium, barium, potassium, sodium, manganese, antimony, and/or lanthanum, which are present in the finished catalyst as salts, e.g. an acetate salt. The preferred salts are potassium or sodium acetate. The co-promoter is preferably present in the catalyst composition in a concentration of 0.1 to 15% by weight of catalyst, more preferably, from 1 to 5% by weight.

Where a liquid acetic acid feed is used the preferred concentration of co-promoter salt is up to 6% by weight, especially 2.5 to 5.5%. Where the acid is introduced in the vapour phase the co-promoter salt is preferably present in a concentration up to 11 wt %.

The catalyst may be a supported catalyst. Suitable catalyst supports include porous silica, alumina, silica/alumina, titania, silica/titania or zirconia. Preferably the support is silica. Suitably, the support may have a pore volume from 0.2 to 3.5 mL per gram of support, a surface area of 5 to 800 $m^2$ per gram of support and an apparent bulk density of 0.3 to 1.5 g/mL.

The catalyst for the production of vinyl acetate may be prepared by any suitable method, such as that detailed in EP-A-0672453, the contents of which are hereby incorporated by reference.

The method of catalyst preparation may be varied to optimise catalyst performance based on maximising vinyl acetate yield and selectivity.

Any suitable method for introducing the catalyst into the fluidised bed of catalyst may be employed. Suitably, the catalyst may be introduced into the fluidised bed of catalyst by the use of an overpressure of a gas such as nitrogen with or without the assistance of gravity. Alternatively, any suitable mechanical means may be used, for example, a screw feeder mechanism.

The overall activity of the vinyl acetate catalyst bed may be determined by any suitable method known in the art, for example, kinetic modeling or analysis of samples of catalyst withdrawn from the bed. Typically, in a fluid bed process for the manufacture of vinyl acetate the production rate of vinyl acetate is suitably determined by calculating the tonnes of vinyl acetate product produced per day.

Suitably, the overall activity of the catalyst bed is monitored regularly, for example, monthly, but if desired monitoring may be more or less frequent.

Generally, the amounts of catalyst to be added to the catalyst bed will depend on the reaction parameters and the activity of the catalyst to be added.

The addition/removal of catalyst to/from the catalyst bed may be used in conjunction with adjustments to the reactor temperature and/or adjustments to the feed composition such as the oxygen concentration. The extent to which adjustments may be made will depend upon the reaction parameters and also safety constraints. Such adjustments can readily be determined by the man skilled in the art. Additional promoter may also be added during the process to maintain overall activity and/or selectivity.

BRIEF DESCRIPTION OF THE DRAWINGS

The invention will now be illustrated by reference to the following Examples and drawings.

EXAMPLES

Example 1

Figure 1:
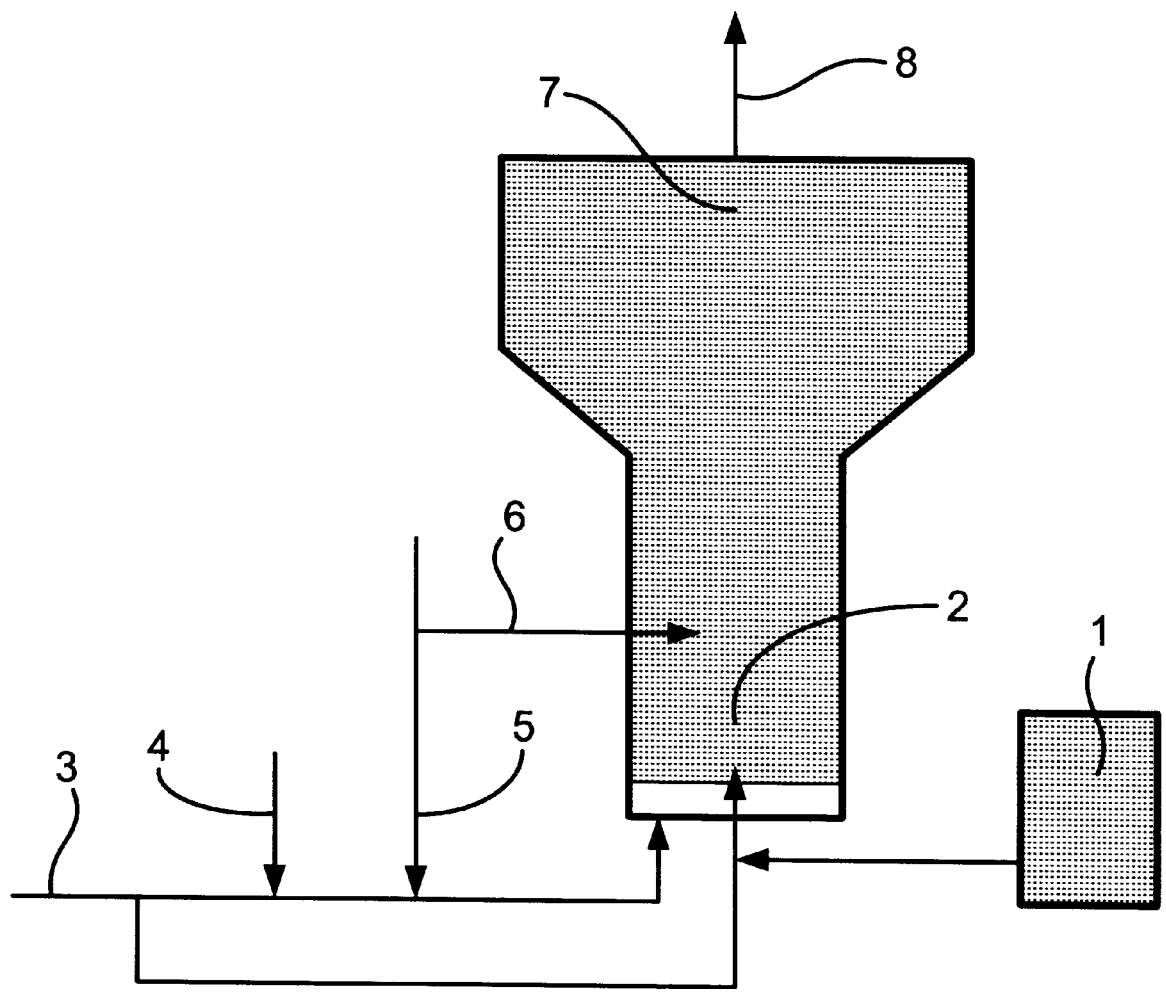
FIG. 1 illustrates a fluidised bed reactor suitable for the production of vinyl acetate.

Fluid Bed Process for the Production of Vinyl Acetate a) Preparation of Support

The support used for the catalyst preparation was prepared by spray-drying a mixture of Nalco (Nalco Chemical Company) silica sol 1060 and Degussa (Degussa Chemical Company) Aerosil® silica. In the dried support, 80% of the silica came from the sol and 20% of the silica came from the Aerosil. The spray-dried microspheres were calcined in air at 640° C. for 4 hours. This method of support preparation is described in EP-A-0 672 453.

The particle size distribution of the support which was used for the catalyst preparation is as follows:

| Particle size | % |
|---|---|
| >300 microns | 2 |
| 88–300 microns | 30 |
| 44–88 microns | 38 |
| <44 microns | 30 | b) Preparation of Catalyst

Silica support (54.4 parts) as prepared in (a) above was impregnated with a solution of $Na_2PdCl_4.xH_2O$ (containing 1 part palladium) and $AuCl_4.xH_2O$ (containing 0.4 parts gold) in distilled water by incipient wetness. The resulting mixture was mixed thoroughly, left to stand for 1 hour and dried overnight.

The impregnated material was added slowly to a 5% solution of hydrazine in distilled water, and the mixture allowed to stand overnight with occasional stirring. Thereafter the mixture was filtered and washed with 4×400 parts distilled water. The solid was then dried overnight. The material was impregnated with an aqueous solution of potassium acetate (2.8 parts) by incipient wetness. The resulting mixture was mixed thoroughly, left to stand I hour and dried overnight.

The catalyst was then screened to provide a suitable particle size distribution.

The resulting catalyst comprised 1.59 wt % palladium, 0.62 wt % gold and 1.9 wt % potassium.

c) Production of Vinyl Acetate

A 14 liter fluidised bed reactor was operated at 8 barg with a uniform bed temperature of 155° C. A schematic representation of the reactor is shown in FIG. 1 and includes a feed system, reactor gas/liquid separation, gas recycle, product recovery and liquid recycle. With reference to FIG. 1, fresh acetic acid from storage (1) and recycle acetic acid are pumped together with some recycle gas (3) to a twin fluid nozzle within the fluid bed (2). The remainder of the recycle gas feed (3), fresh ethylene (4) and oxygen (5) enter the plenum and through a sintered plate into the reactor. Fresh oxygen (6) may be fed directly into the fluid bed. A freeboard section is provided for disengaging the catalyst (7). The gaseous products exit the reactor through exit (8). The reactor temperature is controlled using a pumped system where hot heat transfer fluid is passed through three jackets (not shown) attached to the reactor wall. All equipment is constructed out of 316L stainless steel.

4.5 kg of catalyst prepared according to step (b) of Example 1 was loaded into the reactor. The total feed composition in to the reactor was controlled between:

Ethylene 55–70 volume %

Acetic Acid 8–12 volume %

Oxygen 3.5–8 volume %

Inerts including carbon dioxide, argon, ethane and methane provided the balance.

A twin fluid nozzle was utilised to introduce the acetic acid in to the reactor with a liquid: gas weight ratio of 2.05:1. The total superficial velocity in the reactor was controlled around 11 to 13.5 cm/s.

Actual overall catalyst activity of the catalyst bed was calculated by matching a predicted production rate using the kinetic rate expressions derived for fresh catalyst with the actual production rate. The kinetic rate expressions were used in an integrated bed model, the predicted production rate was also corrected for the amount of catalyst present in the reactor.

Actual Vinyl Acetate Production Rate=Catalyst Activity*Kinetics

Figure 2:
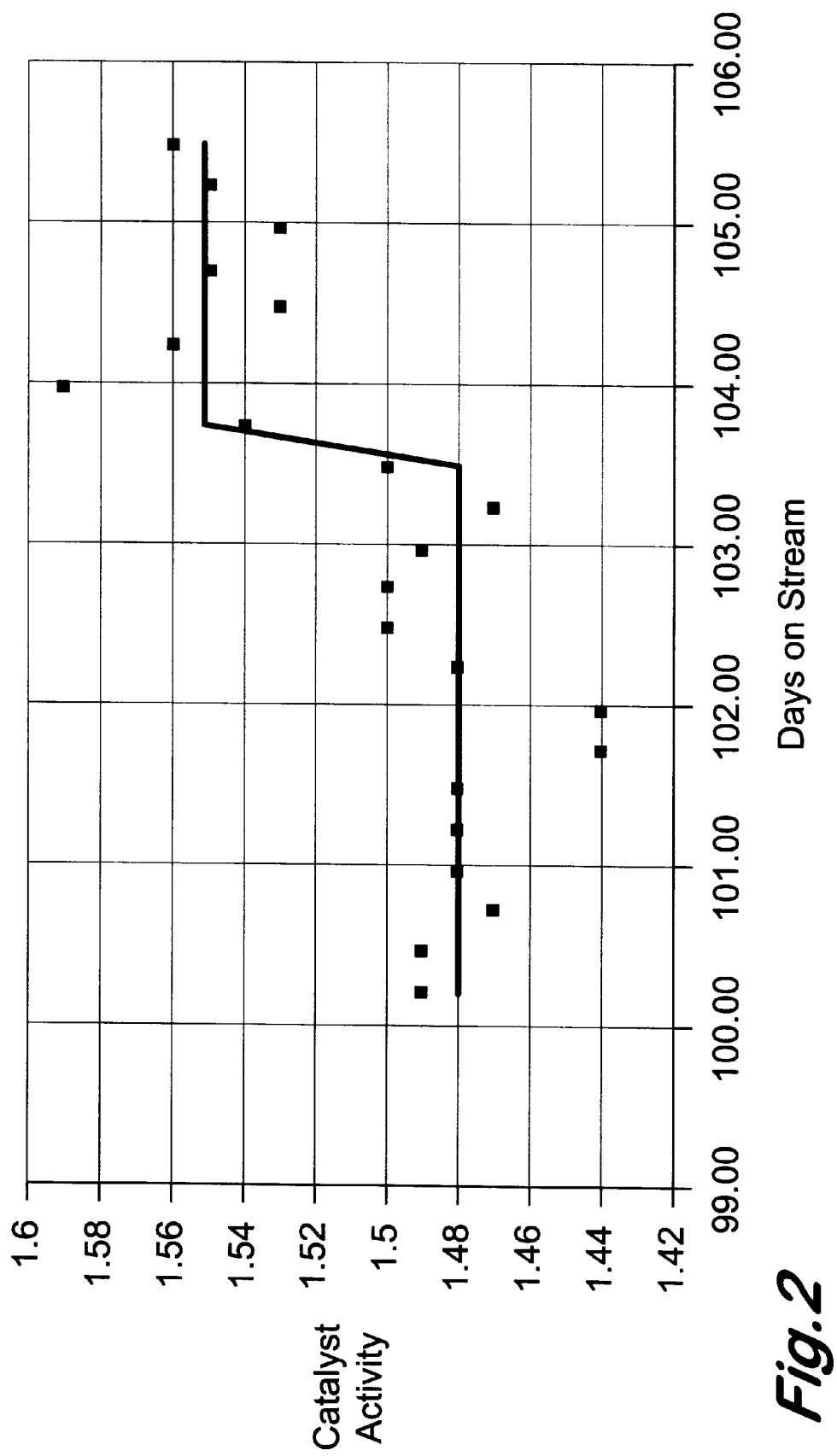
FIG. 2 is a graph illustrating the effect of the addition of fresh catalyst to a fluidised bed of catalyst on overall catalyst activity in the production of vinyl acetate.

The process was operated under the conditions described above for 79 days and then a further 100 g of fresh catalyst was added to the reactor. After 103 days of operation a further 200 g of fresh catalyst was added to the reactor. FIG. 2 below shows the increase in activity corresponding to this last addition of catalyst from an average activity of 1.48 to 1.55.

Example 2

To obtain a greater increase in overall catalytic activity than the increase obtained by the addition of fresh catalyst which has the same activity as the initial activity of the catalyst bed, Example 1 may be repeated using as added catalyst, a catalyst of higher activity than the initial activity of the catalyst in the fluidised bed.

I claim:

1. A process for the fluid bed production of vinyl acetate which comprises reacting ethylene, acetic acid and an oxygen-containing gas in a fluid bed reactor at elevated temperature in the presence of a fluidised bed of catalyst, in which process, catalyst is added to said fluidised bed of catalyst, wherein the overall catalytic activity of the fluidised bed of catalyst is controlled to a pre-determined value by adjusting the activity of said added catalyst and/or adjusting the rate of addition of said added catalyst.

2. A process as claimed in claim 1 in which the added catalyst has a different activity than the initial activity of the catalyst in the fluidised bed.

3. A process as claimed in claim 2 in which the added catalyst has a higher activity than the initial activity of the catalyst in the fluidised bed.

4. A process as claimed in claim 3 in which the added catalyst has a higher active metal loading than the catalyst in the fluidised bed.

5. A process as claimed in claim 2 in which the added catalyst has a lower activity than the initial activity of the catalyst in the fluidised bed.

6. A process as claimed in claim 5 in which the added catalyst has a lower active metal loading than the catalyst in the fluidised bed.

7. A process as claimed in claim 5 in which the added catalyst is diluted with inert support material.

8. A process as claimed in claim 1 in which the overall catalytic activity of the fluidised bed of catalyst is controlled to a pre-determined value by increasing the rate of addition of said added catalyst.

9. A process as claimed in claim 8 which further comprises decreasing the rate of removal of catalyst from the fluidised bed.

10. A process as claimed in claim 1 in which the overall catalytic activity of the fluidised bed of catalyst is controlled to a pre-determined value by decreasing the rate of addition of said added catalyst.

11. A process as claimed in claim 10 which further comprises increasing the rate of removal of catalyst from the fluidised bed.

12. A process for the fluid bed production of vinyl acetate which comprises reacting ethylene, acetic acid and an oxygen-containing gas in a fluid bed reactor at elevated temperature in the presence of a fluidised bed of catalyst, in which process, catalyst is added to said fluidised bed of catalyst, wherein the overall production rate of the process is adjusted to a pre-determined value by adjusting the activity of said added catalyst and optionally adjusting the rate of addition of said added catalyst.

13. A process as claimed in claim 12 in which the added catalyst has a different activity than the initial activity of the catalyst in the fluidised bed.

14. A process as claimed in claim 13 in which the added catalyst has a higher activity than the initial activity of the catalyst in the fluidised bed.

15. A process as claimed in claim 14 in which the added catalyst has a higher active metal loading than the catalyst in the fluidised bed.

16. A process as claimed in claim 13 in which the added catalyst has a lower activity than the initial activity of the catalyst in the fluidised bed.

17. A process as claimed in claim 16 in which the added catalyst has a lower active metal loading than the catalyst in the fluidised bed.

18. A process as claimed in claim 16 in which the added catalyst is diluted with inert support material.

\* \* \* \* \*